United States Patent [19]

Steffen

[11] Patent Number: 5,569,780
[45] Date of Patent: Oct. 29, 1996

[54] DIALKYL 2-HALOETHYL MALONATES

[75] Inventor: Klaus-Dieter Steffen, Hennef, Germany

[73] Assignee: Hüls Aktiengesellschaft, Marl, Germany

[21] Appl. No.: 493,169

[22] Filed: Jun. 21, 1995

Related U.S. Application Data

[62] Division of Ser. No. 287,157, Aug. 8, 1994, Pat. No. 5,463,111.

[30] Foreign Application Priority Data

Aug. 11, 1993 [DE] Germany .......................... 43 26 918.4

[51] Int. Cl.$^6$ .................................................... C07C 69/38
[52] U.S. Cl. ................................................................ 560/192
[58] Field of Search ............................................. 560/192

[56] References Cited

U.S. PATENT DOCUMENTS 5,241,059  8/1993  Yoshinaga ................................ 536/4.1

Primary Examiner—Samuel Barts
Attorney, Agent, or Firm—Felfe & Lynch

[57] ABSTRACT

Novel dialkyl 2-haloethyl malonates are prepared from a dialkyl cyclopropane-1,1-dicarboxylate by reaction with a hydrogen halide in the presence of a 1,2-dialkoxy ethane as a solvent and of a Friedel-Crafts catalyst.

1 Claim, No Drawings

DIALKYL 2-HALOETHYL MALONATES

This application is a division of copending application Ser. No. 08/287,157, filed Aug. 8, 1994 now U.S. Pat. No. 5,463,111.

FIELD OF THE INVENTION

This invention relates to a novel method of preparing a dialkyl 2-haloethyl malonate by reacting a dialkyl cyclopropane-1,1-dicarboxylate with an hydrogen halide in the presence of a solvent and a catalyst.

More particularly, the present invention relates to an improved method for the preparation of a dialkyl 2-haloethyl malonate of the formula

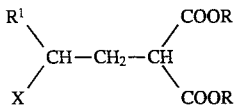

wherein

R is alkyl of 1 to 10 carbon atoms, $R^1$ is hydrogen, methyl, ethyl or vinyl, and X is chlorine, bromine or iodine, by reacting a dialkyl cyclopropane-1,1-dicarboxylate of the formula

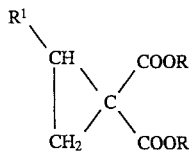

wherein

R and $R^1$ have the meanings defined above, with an hydrogen halide of the formula

HX wherein X has the meanings defined above, in the presence of a 1,2-dialkoxy ethane solvent and a Friedel-Crafts catalyst.

BACKGROUND OF THE INVENTION

The alkylation of esters of malonic acid at the central carbon atom is usually carried out by reacting an ester of malonic acid with an alkyl halide in the presence of a stoichiometric amount of an alkali metal alkoxide, accompanied by the release of the corresponding alkali metal halide. However, if an attempt is made to prepare an ester of a 2-haloethyl malonic acid by this method, for instance the preparation of diethyl 2-chloroethyl malonate by reacting diethyl malonate with sodium ethoxide and 1,2-dichloroethane, it becomes quickly apparent that this method is not feasible.

For this reason, a different method is employed in the literature, namely the cleavage of the 1,1-dicarbalkoxycyclopropane ring with a gaseous hydrogen halide (see N. Demjanov et al, Chem. Zentralblatt 1939 II, 2913; and A. C. Knipe et al, J. of Chem. Soc. 1968, 67 to 71).

Thus, Demjanov et al were the first to prepare diethyl-β-chloroethyl malonate (in addition to ethyl cyclopropane-1-carboxamide-1-carboxylate) from ethyl cyclopropane-1-cyano-1-carboxylate with hydrogen chloride in aqueous ethanol. Knipe et al opened the 1,1-dicarbethoxy cyclopropane ring with hydrogen bromide to form diethyl β-bromoethyl malonate, which they converted into the corresponding chloroethyl malonate by reaction with lithium chloride.

These processes, however, are awkward to perform, produce low yields and are not suitable for a cost-effective preparation of the desired end product.

1,1-cyclopropane dicarboxylates can, inter alia, be prepared according to J. Heiszmann (Synthesis 1987, 738).

The preferred solvent for reactions with esters is the corresponding alcohol with which the acid forms the ester, i.e. in the case of dimethyl cyclopropane-1,1-dicarboxylate the preferred solvent is methanol. However, when 1 mol of dimethyl cyclopropane-1,1-dicarboxylate is dissolved in methanol and 2 mols of hydrogen chloride are introduced into the solution, no reaction of any kind takes place even after 5 hours at 60° C. When aluminum chloride is then added as a catalyst, the cyclopropane ring does open but the reaction subsides after the conversion is only from ⅔ to ¾ complete. The reason for this is the undesired formation of methyl chloride and water. The water destroys the catalyst and terminates its action.

OBJECTS OF THE INVENTION

It is an object of the present invention to provide a solvent for the above mentioned reaction in which hydrogen chloride and the catalyst are freely soluble but which does not react with the catalyst or with the ester.

Other objects of the present invention will become apparent as the description thereof proceeds.

DESCRIPTION OF THE INVENTION

The above object is achieved in accordance with the present invention by performing the reaction in a 1,2-dialkoxy ethane as the solvent medium, specifically dimethoxy ethane or diethoxy ethane, the boiling points of which are also sufficiently widely separated from those of the target products. It is not difficult to dissolve 20% to 30% by weight of hydrogen chloride in dimethoxy ethane. After completion of the reaction the solvent is distilled off together with the excess hydrogen chloride and is recycled. 100 g to 500 g of solvent are provided for 1 mol of the cyclopropane ester.

Friedel-Crafts catalysts are used as catalysts. Aluminum chloride is preferred, but other catalysts such as zinc chloride, stannic chloride and boron trifluoride may also be used. The catalyst is used in amounts of 0.025% to 0.5% by weight, preferably 0.05% to 0.2% by weight, based on the total weight of the reaction mixture.

The hydrogen chloride is provided in excess of 5% to 100%, preferably of 30% to 50%. The excess can be reused together with the solvent for subsequent batches.

The reaction rate is lowest for dimethyl cyclopropane-1,1-dicarboxylate and increases with esters of higher alcohols, for example ethanol or propanol. A reaction time of 5 hours is sufficient at a reaction temperature of 40° to 60° C. If the reaction is to be carried out at room temperature, a greater number of hours has to be counted on. In general, the reaction is performed at 0° to 100° C., preferably 20° to 50° C. After completion of the reaction a possible turbidity can be removed by filtration. Thereafter the reaction mixture is worked up by distillation, the solvent and the hydrogen chloride distilling over first, and the target product is then distilled off under reduced pressure.

If it is desired to prepare a 2-iodoethyl malonate from the corresponding 2-chloroethyl malonate, this can easily be accomplished by way of the Finckelstein reaction [Ber 43, 1528 (1910)]. For this purpose the chloro-compound is added to a solution of sodium iodide in acetone (23% sodium iodide soluble), the precipitated sodium chloride is filtered off, and the filtrate is worked up by distillation.

The dialkyl 2-haloethyl maionates are useful as intermediates in the preparation of pharmaceutical products.

Some of the end products of the process according to the present invention are novel compounds. The novel compounds are the following:
dimethyl 2-chloroethyl malonate,
diisopropyl-2-chloroethyl malonate,
di-n-butyl-2-chloroethyl malonate,
dimethyl 2-chloroethyl-2-vinyl malonate,
dimethyl 2-iodoethyl malonate, and
diethyl 2-iodoethyl malonate.

The following examples illustrate the present invention and will enable others skilled in the art to understand it more completely. It should be understood, however, that the invention is not limited solely to the particular examples given below.

EXAMPLE 1

Preparation of dimethyl 2-chloroethyl malonate 200 g of 1,2-dimethoxy ethane are placed into a 1 liter multi-neck flask equipped with a stirrer, thermometer, cooler and gas inlet tube, and 55 g of hydrogen chloride (1.5 mols) are introduced into the flask. 158.1 g of dimethyl cyclopropane-1,1-dicarboxylate (1.0 mol) and 0.4 g of aluminum chloride were then dissolved in the contents of the flask, and the solution was stirred for 5 hours at 50° C. The clear solution was then worked up by distillation in a column. After distilling off the 1,2-dimethoxy ethane and the excess hydrogen chloride, both of which can be used again in subsequent batches, the target product was distilled off at 85° C./5 mbar.
Yield: 183.2 g (93.3% of theory)
Purity: 99.1% (GC)
Flash point: 120°±2° C.

EXAMPLE 2

Preparation of diethyl 2-chloroethyl malonate 73 g of hydrogen chloride (2.0 mols) were introduced into 300 g of 1,2-diethoxy ethane, 186 g of diethyl cyclopropane-1,1-dicarboxylate (1.0 mol) and 0.5 g of aluminum chloride were added to the contents of the flask, and the mixture was stirred overnight (16 hours) at room temperature (about 20° C.). The reaction mixture was then worked up by distillation in a column. After removing the solvent and the excess hydrogen chloride, the target product was separated in vacuo.
Boiling point: 87° C./1 mbar
Yield: 196.5 g (87% of theory)
Purity: 98.5% (GC)

EXAMPLE 3

Preparation of dimethyl 2-vinyl-2-chloroethyl malonate (3-chloro-5,5-dicarbomethoxy-1-pentene)

400 g of 1,2-dimethoxy ethane were introduced into a 1 liter glass flask equipped with a stirrer and a thermometer and admixed with 69 g of gaseous hydrogen chloride. 184.1 g of 1-vinyl- 2,2-dicarbomethoxy cyclopropane (93.7% pure, 0.937 mol) and 0.65 g of aluminum chloride were then added to the contents, and the mixture was stirred. The temperature of the mixture rose to 40° C. The reaction was allowed to go to completion by letting the mixture stand overnight. After filtering off a slight turbidity, the reaction mixture was distilled in a 70 cm column. After collecting the 1,2-dimethoxy ethane which distilled over first and became available for reuse as a solvent in subsequent batches, the target product distilled over in pure form at 87° C./0.8 mbar.
Yield: 177 g (85.9% of theory)
Purity: 98.2% (GC)
The identity of the end product was confirmed by mass spectra (M=220, 222) and 1-H and 13-C NMR spectra.

EXAMPLE 4

Preparation of diisopropyl 2-chloroethyl malonate 73.0 g of gaseous hydrogen chloride (2.0 mols) were dissolved in 350 g of 1,2-dimethoxy ethane, and then 214.1 g of diisopropyl cyclopropane-1,1-dicarboxylate (1 mol) and 0.7 g of aluminum chloride were added to the solution, and the reaction mixture was stirred for 5 hours at 50° C. The slight turbidity in the reaction solution was filtered off, and the filtrate was distilled in a column. The 1,2-dimethoxy ethane solvent which passed over first was separated, and the target product distilled over at the boiling point of 90° C./0.9 mbar.
Yield: 200.7 g (80.2% of theory)
Purity: 99.4% (GC).
The identity of the reaction product was confirmed by mass spectra (M=250/252) and 1-H and 13-C NMR spectra.

EXAMPLE 5

Preparation of di-n-butyl 2-chloroethyl malonate 73.0 g gaseous hydrogen chloride (2.0 mols) were introduced into 300 g of 1,2-dimethoxy ethane, 242.1 g of di-n-butyl cyclopropane-1,1-dicarboxylate (1.0 mol) and 0.7 g of aluminum chloride were added, and the resulting reaction mixture was stirred for 8 hours at 50° C. After filtering off a slight turbidity, the reaction mixture was separated by distillation in a column. After the 1,2-dimethoxy ethane which passed over first was collected, the target product distilled over at the boiling point of 128° C./2 mbar.
Yield: 228.7 g (82.1% of theory)
Purity: 98.7% (GC).
The identity of the reaction product was confirmed by mass spectrum (M=278/280) and 1-H and 13-C NMR spectra.

EXAMPLE 6

Preparation of dimethyl 2-iodoethyl malonate 41.8 g of sodium iodide (0.279 mol) were dissolved in 145 g of acetone, 49.4 g of dimethyl 2-chloroethyl malonate (0,254 mol) were added to the solution, and the mixture was stirred for 37 hours at 50° C. Thereafter, the precipitated sodium chloride was filtered off, the acetone was distilled off, and the remaining crude reaction product was distilled under an oil pump vacuum. The distillate turned brown due to the onset of decomposition.
Boiling Point: 110° C./from 1 to 2 mbar
Purity: 97% (GC).

The identity of the reaction product was confirmed by mass and NMR spectra.

EXAMPLE 7

Preparation of diethyl 2-iodoethyl malonate 41.8 g of sodium iodide (0.279 mol) were dissolved in 145 g of acetone, 56.5 g of diethyl 2-chloroethyl malonate (0.254 mol) were added to the solution, and the mixture was stirred for 8 days at room temperature. Thereafter, the precipitated sodium chloride was filtered off, and the acetone was completely distilled out. The crude reaction product distilled over at 107° to 109° C./0.5 mbar. The oily distillate turned brown due to the onset of decomposition.
Purity: 96% (GC)

The identity of the reaction product was confirmed by mass and NMR spectra.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. A dialkyl 2-haloethyl malonate selected from the group consisting of dimethyl 2-chloroethyl malonate, diisopropyl 2-chloroethyl malonate, di-n-butyl 2-chloroethyl malonate, and dimethyl 2-chloroethyl-2-vinyl malonate.

* * * * *